US009162959B2

(12) United States Patent
Kiely et al.

(10) Patent No.: US 9,162,959 B2
(45) Date of Patent: *Oct. 20, 2015

(54) METHOD OF OXIDATION USING NITRIC ACID

(71) Applicant: The University of Montana, Missoula, MT (US)

(72) Inventors: Donald E. Kiely, Missoula, MT (US); Kirk R. Hash, Sr., Drummond, MT (US)

(73) Assignee: The University of Montana, Missoula, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/150,633

(22) Filed: Jan. 8, 2014

(65) Prior Publication Data

US 2014/0256983 A1   Sep. 11, 2014

Related U.S. Application Data

(63) Continuation of application No. 12/753,721, filed on Apr. 2, 2010, now abandoned, which is a continuation of application No. 11/890,760, filed on Aug. 6, 2007, now Pat. No. 7,692,041.

(60) Provisional application No. 60/836,329, filed on Aug. 7, 2006.

(51) Int. Cl.
*C07C 51/00* (2006.01)
*C07C 51/27* (2006.01)

(52) U.S. Cl.
CPC ............... *C07C 51/27* (2013.01); *C07C 51/00* (2013.01)

(58) Field of Classification Search
CPC ........ C07C 51/00; C07C 51/316; C07C 51/27
See application file for complete search history.

(56) References Cited

U.S. PATENT DOCUMENTS

| | | | |
|---|---|---|---|
| 1,520,885 A | 12/1924 | Rankin | |
| 2,314,831 A | 3/1943 | Kamlet | |
| 2,380,196 A | 7/1945 | Solomon | |
| 2,419,019 A * | 4/1947 | Hales | 562/531 |
| 2,436,659 A | 2/1948 | Mehltretter et al. | |
| 2,472,168 A | 6/1949 | Mehltretter | |
| 2,529,177 A | 11/1950 | Nieland | |
| 2,529,178 A | 11/1950 | Nieland | |
| 3,242,207 A | 3/1966 | Ulrich et al. | |
| 3,346,623 A | 10/1967 | Young | |
| 3,362,885 A | 1/1968 | Harned | |
| 3,589,859 A | 6/1971 | Foroulis | |
| 3,652,396 A | 3/1972 | Tanaka | |
| 3,711,246 A | 1/1973 | Foroulis | |
| 3,798,168 A | 3/1974 | Tumerman et al. | |
| 3,819,659 A | 6/1974 | Baldwin et al. | |
| 3,951,877 A | 4/1976 | Okumura et al. | |
| 4,000,083 A | 12/1976 | Heesen | |
| 4,108,790 A | 8/1978 | Foroulis | |
| 4,120,655 A | 10/1978 | Crambes | |
| 4,129,423 A | 12/1978 | Rubin | |
| 4,485,100 A | 11/1984 | Hochstrasser et al. | |
| 4,512,552 A | 4/1985 | Katayama et al. | |
| 4,833,230 A | 5/1989 | Kiely et al. | |
| 4,834,793 A | 5/1989 | Schneider et al. | |
| 4,845,123 A | 7/1989 | Walaszek | |
| 5,017,485 A | 5/1991 | Bringer-Meyer | |
| 5,256,294 A | 10/1993 | van Reis | |
| 5,264,123 A | 11/1993 | Bailey | |
| 5,312,967 A | 5/1994 | Kiely et al. | |
| 5,329,044 A | 7/1994 | Kiely et al. | |
| 5,330,683 A | 7/1994 | Sufrin | |
| 5,364,644 A | 11/1994 | Walaszek | |
| 5,376,499 A | 12/1994 | Hammerschmidt et al. | |
| 5,434,233 A | 7/1995 | Kiely et al. | |

(Continued)

FOREIGN PATENT DOCUMENTS

| | | |
|---|---|---|
| CA | 2188063 | 4/1998 |
| CN | 1131651 | 9/1996 |

(Continued)

OTHER PUBLICATIONS

Zaragoza Dorwald, Side Reactions in Organic Synthesis, 2005, Wiley-VCH Verlag GmbH & Co. KGaA, Weinheim, Preface. p. IX.*
United States Patent Office Action for U.S. Appl. No. 13/452,560 dated Dec. 4, 2013 (11 pages).
United States Patent Office Action for U.S. Appl. No. 13/586,953 dated Jan. 27, 2014 (7 pages).
Abbadi et al., New Ca-Sequestering Materials Based on the Oxidation of the Hydrolysis Products of Lactose, Green Chem, 1999, 231-235.
Abd El Kader, J.M. et al., "Corrosion inhibition of mild steel by sodium tungstate in neutral solution. Part 3. Coinhibitors and synergism," British Corrosion Journal, 33, 152-157 (1998) Chem Abstr AN 1998:796697.

(Continued)

Primary Examiner — Paul A Zucker
(74) Attorney, Agent, or Firm — Lisa V. Mueller; Michael Best & Friedrich LLP

(57) ABSTRACT

A controlled nitric acid process employing oxygen and nitric acid as co-oxidants is used to oxidize organic compounds subject to nitric acid oxidation, to their corresponding carboxylic acids. Oxidation of some carbohydrates by this process can produce one or more of their corresponding acid forms. The process is carried out at moderate temperatures, typically in the range of 20° C. to 45° C. in a closed reactor, with oxygen gas being introduced into the reaction chamber as needed in order to sustain the reaction. Computer controlled reactors allow for careful and reproducible control of reaction parameters. Nitric acid can be recovered by a distillation/evaporation process, or by diffusion dialysis, the aqueous solution made basic with inorganic hydroxide, and the residual inorganic nitrate removed using a filtration (nanofiltration) device. The method eliminates issues of thermal control of the oxidation, release of nitrogen into the atmosphere, and post-reaction difficulties in the removal of nitric acid and inorganic nitrates.

50 Claims, No Drawings

(56) References Cited

U.S. PATENT DOCUMENTS

| | | |
|---|---|---|
| 5,473,035 A | 12/1995 | Kiely et al. |
| 5,478,374 A | 12/1995 | Kiely |
| 5,531,931 A | 7/1996 | Koefod |
| 5,561,160 A | 10/1996 | Walaszek |
| 5,562,828 A | 10/1996 | Olsen et al. |
| 5,599,977 A * | 2/1997 | Kiely et al. ............... 562/523 |
| 5,891,225 A | 4/1999 | Mishra |
| 5,958,867 A | 9/1999 | Lamberti et al. |
| 5,999,977 A | 12/1999 | Riddle |
| 6,049,004 A | 4/2000 | Kiely et al. |
| 6,156,226 A | 12/2000 | Klyosov et al. |
| 6,372,410 B1 | 4/2002 | Ikemoto et al. |
| 6,498,269 B1 | 12/2002 | Merbouh et al. |
| 6,686,325 B2 | 2/2004 | Ruhr et al. |
| 6,831,195 B2 | 12/2004 | Nishimura et al. |
| 6,843,931 B2 | 1/2005 | Sapienza |
| 6,861,009 B1 | 3/2005 | Leist |
| 6,894,135 B2 | 5/2005 | Kiely et al. |
| 6,919,478 B2 | 7/2005 | Kawato et al. |
| 7,125,441 B1 | 10/2006 | Furman et al. |
| 7,314,906 B2 | 1/2008 | Kiely et al. |
| 7,658,861 B2 | 2/2010 | Koefod |
| 7,692,041 B2 | 4/2010 | Kiely |
| 8,153,573 B2 | 4/2012 | Miralles et al. |
| 8,623,943 B2 | 1/2014 | Kiely |
| 8,679,364 B2 | 3/2014 | Pylkkanen |
| 2003/0109394 A1 | 6/2003 | Ruhr et al. |
| 2003/0168625 A1 | 9/2003 | Sapienza et al. |
| 2003/0176305 A1 | 9/2003 | Hoyt et al. |
| 2004/0025908 A1 | 2/2004 | Douglas et al. |
| 2004/0028655 A1 | 2/2004 | Nelson et al. |
| 2004/0185562 A1 | 9/2004 | Schroeder et al. |
| 2005/0202981 A1 | 9/2005 | Eveland et al. |
| 2005/0202989 A1 | 9/2005 | Wilson |
| 2005/0230658 A1 | 10/2005 | Koefod |
| 2007/0037727 A1 | 2/2007 | Fiore et al. |
| 2007/0278446 A1 | 12/2007 | Koefod |
| 2008/0033205 A1 | 2/2008 | Kiely et al. |
| 2008/0099716 A1 | 5/2008 | Koefod |
| 2008/0287334 A1 | 11/2008 | Smith et al. |
| 2008/0302737 A1 | 12/2008 | Denkewicz, Jr. et al. |
| 2009/0250653 A1 | 10/2009 | Kiely |
| 2010/0041574 A1 | 2/2010 | Warkotsch et al. |
| 2010/0130774 A1 | 5/2010 | Wan et al. |
| 2010/0191002 A1 | 7/2010 | Kiely |
| 2011/0263905 A1 | 10/2011 | Purola |
| 2011/0269662 A1 | 11/2011 | Miralles |
| 2012/0035356 A1 | 2/2012 | Kiely |
| 2012/0119152 A1 | 5/2012 | Smith |
| 2012/0277141 A1 | 11/2012 | Smith |
| 2012/0295986 A1 | 11/2012 | Smith |
| 2012/0305832 A1 | 12/2012 | Kiely |
| 2014/0275621 A1 | 9/2014 | Donen |
| 2014/0275622 A1 | 9/2014 | Donen |
| 2014/0275623 A1 | 9/2014 | Donen |

FOREIGN PATENT DOCUMENTS

| | | |
|---|---|---|
| CN | 1970488 | 5/2007 |
| DE | 2016686 | 11/1970 |
| DE | 1929968 | 12/1970 |
| DE | 117492 | 1/1976 |
| DE | 3331751 | 3/1984 |
| DE | 3519884 | 1/1986 |
| EP | 0652305 | 5/1995 |
| EP | 0758678 | 2/1997 |
| EP | 0819653 | 1/1998 |
| EP | 1201617 | 5/2002 |
| FR | 2054945 | 6/1971 |
| FR | 2115300 | 8/1972 |
| GB | 866840 | 5/1961 |
| GB | 2405636 | 9/2003 |
| JP | 47048091 | 12/1972 |
| JP | S51011030 | 1/1976 |
| JP | 51041578 | 11/1976 |
| JP | 54043840 | 4/1979 |
| JP | S57192270 | 11/1982 |
| JP | S58091174 | 5/1983 |
| JP | 60-50188 | 3/1985 |
| JP | S60050188 | 3/1985 |
| JP | 60108352 | 6/1985 |
| JP | 60112676 | 6/1985 |
| JP | 63248782 | 10/1988 |
| JP | 04214057 | 8/1992 |
| JP | H06306652 | 11/1994 |
| JP | H09104687 | 4/1997 |
| JP | 2003306369 | 10/2003 |
| JP | 2004123465 | 4/2004 |
| JP | 2008054806 | 3/2008 |
| KR | 20020066275 | 8/2002 |
| PL | 98149 | 8/1978 |
| RO | 69880 | 4/1981 |
| WO | 92/07108 | 4/1992 |
| WO | WO 00/34221 | 6/2000 |
| WO | WO 2004/052958 | 6/2004 |
| WO | WO 2004/052959 | 6/2004 |
| WO | WO 2008/021054 | 2/2008 |
| WO | WO 2009/065143 | 5/2009 |
| WO | WO 2012/065001 | 5/2012 |
| WO | WO 2012/145688 | 10/2012 |
| WO | WO 2012/145690 | 10/2012 |
| WO | WO 2013/090090 | 6/2013 |

OTHER PUBLICATIONS

Abdallah, M. "Sodium gluconate, triethanolamine and their mixtures as corrosion inhibitors of carbon steel in 3.5% NaCl solution," Journal of the Electrochemical Society of India, 48, 121-127, (1999) Chem Abst AN 1999:374923.

Allcock, H.R. et al., "Effect of nonstoichiometric reactant ratios on linear condensation polymers," Contemporary Polymer Chemistry, 2nd Edition, Prentice-Hall, New Jersey (1990) Part II, 274-275.

Billmeyer, F.W., Jr., "Molecular weight and molecular-weight distribution," Textbook of Polymer Science, 3rd Edition, Wiley Interscience, New York (1984) 38-47.

Cantrell, C. E., et al., "s-Dicarbonyl Sugars. 5. A Novel Synthesis of a Branched-Chain Cyclitol," J. Org. Chem. (1977) 42(22):3562-3567.

Carter, Andy, "Modifications in the Preparation of Glucaric Acid and Some 4-alkyl-4-azaheptane-1,7-diamines," 1998, Thesis, University of Alabama, Birmingham, AL, p. 18-20.

Chen, L., "Experimental and Theoretical Studies Concerned with Synthetic Acyclic Carbohydrate Based Polyamides," A Dissertation, University of Alabama at Birmingham (1992).

Chen, L. et al., "Synthesis of steroregular head-tail hydroxylated nylons derived from D-glucose," J. Org. Chem. (1996) 61:5847-5851.

Collepardi, M.M.; "Concrete Admixture Handbook: Properties, Science and Technology", 2nd Edition, Ramachandran,V.S. Editor,Noyes Publications, Park Ridge,NJ (1995) p. 286-409.

Cotton, F.A. et al., Advanced Inorganic Chemistry, 1988, p. 341-353, John Wiley and Sons, New York.

CRC Handbook of Chemistry and Physics, edited by Weast et al., 64th Edition, 1983-84, Boca Raton, Florida, p. B-117.

Hashimoto et al., "Macromolecular synthesis from cacchari lactones. Ring-opening polyaddition of D-glucaro- and D-mannaro-1,4:6,3-dilactones with alkylenediamines," J. Polym. Sci. Part A: Polym. Chem. (1993) 31:3141-3149.

Hashimoto, K. et al., "Ring-opening polyaddition of D-glucaro-1,4:6,3-dilactone with p-zylylenediamine," Macromol. Chem. Rapid Commun. (1990) 11:393-396.

Haworth et al., "Lactones of mannosaccharic acid, Part I. 2: 5-dimethyl Δ4-manno-saccharo-3: 6-lactone 1-methyl ester, an analogue of ascorbic acid," J. Chem. Soc. London (1944) 56:217-224.

Haworth, W.N. et al., "Some Derivatives of Glucosaccharic Acids," J. Chem. Soc. (1944) 25:65-76.

Kiely et al., "Hydroxylated nylons based on unprotected esterified D-glucaric acid by simple condensation reactions," J. Am. Chem. Soc. (1994) 116(2):571-578.

(56) References Cited

OTHER PUBLICATIONS

Kirk-Othmer Encyclopedia of Chemical Technology, 3rd Edition, Wiley, New York, vol. 16, 617-634, "Hydrocarbon Resins" to "Hypnotics, Sedatives, Anticonvulsants".
Korzh, E.N. et al., "Acidity and corrosion activity of brine refrigeratnts based on calcium chloride," Zhurnal Prikladnoi Khimii Journal (Russian) (1981) 54:2404-2407, Chem. Abstr. AN 1982-147045.
Lachman, A., "Dihydroxy-Tartaric Acid," Amer. Chem. Soc. (1921) 43:2091-2097.
Lewis, B.A. et al., Chapter 13, "Galactaric acid and its derivatives," Methods in Carbohydrate Chemistry, R.L. Whistler et al., editors, (1953) II:38-46.
Lin, "Diverse Applications of Carbohydrate Acids in Organic Synthesis," a Dissertation, University of Alabama at Birmingham (1987) p. 48-50, 72-74.
Lowe et al., Soaps and Detergents—The Inorganic Components, J. Am. Oil Chem. Soc., 1978, 55, 32-35.
Mainhardt, H., "N20 Emissions from Adipic Acid and Nitric Acid Production," IPCC Good Practice Guidance and Uncertainty Management in National Greenhouse Gas Inventories (2001).
Marukame, K., S.Fushoku Burnon Iinkai Shiryo(Nippon Xairyo Gakkai), Journal written in Japanese, 173, 1-8, (1993) Chem. Abstr. AN 1993:543767.
Mehletretter, C.L., "D-Giucaric Acid," Methods in Carbohydrate Chemistry, 1963, p. 46-48, vol. II, Academic Press, New York.
Mehltretter, C.L. et al., "Saccharic and Oxalic Acids by the Nitric Acid Oxidation of Dextrose," Agric. and Food Chem. (1953) 1(12):779-783.
Merbough, N. et al., "4-AcNH-tempo-Catalyzed Oxidation of Aldoses to Aldaric Acids Using Chlorine or Bromine as Terminal Oxidants," J. Carbohydr. Chem., 2002, 21:.66-77.
Mor, E. et al., "Steel corrosion inhibition in seawater by calcium organic compounds," Annali deii'University di Ferrara, Sezione 5; Chimica Pura ed Applicata, Journal in French (1971),Chem Abstr AN 1971:414090.
Mor, E. et al., "Zinc gluconate as an inhibitor of the corrosion of mild steel in sea water," Lab Corros. Mar. Met, British Corrosion Journal (1976) 11:199-203 Chem. Abstr. AN 1977:129710.
Mustakas, G.C. et al., "Potassium Acid Saccharate by Nitric Acid Oxidation of Dextrose," Industrial and Engineering Chemistry, Mar. 1954, 427-434.
National Association of Corrosion Engineers (NACE) Standard TM0169-95 as Modified by the Pacific Northwest States, Test Method B, Revision (Apr. 2006).
Ogata, N. et al., "Active polycondensation of diethyl 2,3,4,5-tetrahydroxyadipate with diamines," J. Polym. Sci. Polym. Chem. Ed. (1976) 14:783-792.
Ogata, N. et al., "Copolycondensation of hydroxyl diesters and active diesters with hexamethylenediamine," J. Polym. Sci. Polym. Chem. Ed. (1977) 15:1523-1526.
Ogata, N. et al., "Polycondensation reaction of dimethyl tartrate with hexamethylenediamine in the presence of various matrices," J. Polym. Sci. Polym. Chem. Ed. (1980) 18:939-948.
Ogata, N. et al., "Synthesis of hydrophilic polyamide by active polycondensation," J. Polym. Sci. Polym. Lett. Ed. (1974) 12:355-358.
Ogata, N. et al., "Synthesis of hydrophilic polymide from L-tartarate and diamines by active polycondensation," J. Polym. Sci. Polym. Chem. Ed. (1975) 13:1793-1801.
Ogata, N. et al., "Synthesis of polyamides through active diesters," J. Polym. Sci., Polym. Chem. Ed. (1973) 11:1095-1105.
Ogata, N. et al., "Synthesis of polyesters from active diesters," J. Polym. Sci. Chem. Ed. (1973) 11:2537-2545.
Ogata, N., "New polycondensation systems," Polym. Prepr. (1976) 17:151-156.
Pamuk et al. "The preparation of D-glucaric acid by oxidation of molasses in packed beds" Journal of Chemical Technology and Biotechnology (2001) 76:186-190.

Roper, H., "Selection oxidation of D-glucose: chiral intermediates for industrial utilization," Starch/Starke (1990) 42(9):342-349.
Stanek, J. et al., "Monosaccharide dicarboxylic acids," The Monosaccharides, Academic Press, New York and London (1963) Chapter XXXII, p. 741-752.
Styron, S.D. et al., "MM3(96) conformational analysis of D-glucaramide and x-ray crystal structures of three D-glucaric acid derivatives—models for synthetic poly(alkylene D-glucaramides)," J. Carb. Chem. (2002) 21(1&2):27-51.
Sukhotin,A.M. et al., "Corrosion inhibitor for steel in calcium chloride solutions," Zashchita Mettalov, Journal in Russion (1982) 18:268-70, Chem Ab 1982:476671.
Van Duin et al., Studies on borate esters. Part 8. Interactions of cations with oxyacid anion-bridged esters of D-glucarate in alkaline media, J. Chem. Soc. Dalton Trans., 1987, 8, 2051-2057.
Van Duin et al., Synergic Coordination of Calcium in Borate-Polyhydroxycarboxylate Systems, Carb. Res., 1987, 162, 65-78.
Van Duin, M. et al., "Studies on borate esters. Part 5. The system glucarate borate calcium (II) as studied by 1H, 11B, and 13C nuclear magnetic resonance spectroscopy," J. Chem. Soc. (1987) 2(4):473-478.
Werpy, T. et al., Top Value Added Chemicals from Biomass, Voil-Results of Screening for Potential, www.osti.gov/bridge, U.S. Dept. of Energy, Oak Ridge, TN (2004) 76 pages.
Wilham et al., Organic Acids as Builders in Linear Alkylbenzene Sulfonate Detergent Formulations, J. Am. Oil Chem. Soc., 1971, 48(11), 682-683.
Wisconsin Biorefiners Development Initiative and references therein, Biorefining Processes-Fermentation of 6-Carbon Sugars and Starchs, www.wisbiorefine.org/proc/ferments.pdr (Feb. 5, 2007).
Wrubl, C. et al., "Zinc gluconate as an inhibitor of the corrosion of copper and zinc in seawater," 1st Corros. Mar Met, British Corrosion Journal (1983) 18:142-147, Chem. Abstr. AN 1984:11228.
Yahiro et al., "Efficient acid production from raw corn starch," J. Fermentation Bioengineering (1997) 84(4):375-377.
International Preliminary Report on Patentability for Application No. PCT/US2007/017493 dated Feb. 10, 2009.
International Preliminary Report on Patentability for Application No. PCT/US2008/083831 dated May 18, 2010 (8 pages).
International Preliminary Report on Patentability for Application No. PCT/US2011/060264 dated May 23, 2013 (8 pages).
International Search Report and Written Opinion for Application No. PCT/US2012/034538 dated Jul. 10, 2012 (11 pages).
International Search Report and Written Opinion for Application No. PCT/US2012/034542 dated Jul. 10, 2012 (10 pages).
International Search Report for Application No. PCT/US2003/039733 dated May 13, 2004 (2 pages).
International Search Report for Application No. PCT/US2007/017493 dated Feb. 12, 2008.
International Search Report for Application No. PCT/US2011/060264 dated Feb. 10, 2012.
United States Patent Office Action for U.S. Appl. No. 11/890,760 dated Apr. 16, 2009 (7 pages).
United States Patent Office Action for U.S. Appl. No. 11/890,760 dated Jul. 25, 2008 (8 pages).
United States Patent Office Action for U.S. Appl. No. 12/272,732 dated Apr. 26, 2011.
United States Patent Office Action for U.S. Appl. No. 12/272,732 dated Aug. 24, 2010.
United States Patent Office Action for U.S. Appl. No. 12/272,732 dated Dec. 9, 2011.
United States Patent Office Action for U.S. Appl. No. 12/272,732 dated Jul. 6, 2012 (12 pages).
United States Patent Notice of Allowance for U.S. Appl. No. 12/272,732 dated Aug. 9, 2013 (9 pages).
United States Patent Office Action for U.S. Appl. No. 14/206,796 dated Nov. 4, 2014 (35 pages).
United States Patent Office Action for U.S. Appl. No. 12/422,135 dated Dec. 17, 2014 (8 pages).
United States Patent Office Action for U.S. Appl. No. 13/294,085 dated Apr. 1, 2015 (15 pages.).
United States Patent Office Action for U.S. Appl. No. 14/107,297 dated Mar. 11, 2015 (4 pages).

(56) References Cited

OTHER PUBLICATIONS

United States Patent Office Notice of Allowance for U.S. Appl. No. 14/089,054 dated Mar. 2, 2015 (7 pages).
U.S. Appl. No. 14/089,054, filed Nov. 25, 2013, Presta.
International Search Report and Written Opinion for Application No. PCT/US2013/071520 dated Feb. 5, 2014 (12 pages).
International Search Report and Written Opinion for Application No. PCT/US2014/024785 dated Jul. 7, 2014 (13 pages).
United States Patent Office Action for U.S. Appl. No. 13/294,085 dated Oct. 3, 2014 (18 pages).
United States Patent Office Action for U.S. Appl. No. 13/452,560 dated Aug. 19, 2014 (10 pages).
United States Patent Office Action for U.S. Appl. No. 13/452,578 dated Sep. 23, 2014 (12 pages).
United States Patent Office Notice of Allowance for U.S. Appl. No. 13/586,953 dated Aug. 7, 2014 (6 pages).
United States Patent Office Action for U.S. Appl. No. 14/089,054 dated Aug. 15, 2014 (16 pages).
United States Patent Office Action for U.S. Appl. No. 14/205,627 dated Aug. 27, 2014 (25 pages).
United States Patent Office Action for U.S. Appl. No. 14/205,832 dated Aug. 27, 2014 (21 pages).
United States Patent Office Action for U.S. Appl. No. 14/727,712 dated Jun. 26, 2015 (14 pages).
United States Patent Office Notice of Allowance for U.S. Appl. No. 14/206,796 dated Jul. 17, 2015 (8 pages).
United States Patent Office Action for U.S. Appl. No. 14/205,832 dated May 12, 2015 (27 pages).
United States Patent Office Action for U.S. Appl. No. 14/205,627 dated May 15, 2015 (28 pages).
United States Patent Office Action for U.S. Appl. No. 14/107,297 dated Jun. 19, 2015 (8 pages).

* cited by examiner

METHOD OF OXIDATION USING NITRIC ACID

CROSS-REFERENCE TO RELATED APPLICATIONS

This application is a continuation of U.S. patent application Ser. No. 12/753,721, filed on Apr. 2, 2010, now abandoned, which is a continuation of U.S. patent application Ser. No. 11/890,760, filed on Aug. 6, 2007, now U.S. Pat. No. 7,692,041, which claims the benefits of U.S. Provisional Patent Application No. 60/836,329, filed Aug. 7, 2006, the contents of all of which are fully incorporated herein by reference.

STATEMENT REGARDING FEDERALLY SPONSORED RESEARCH OR DEVELOPMENT

This invention was made with Government support under Grant No. 2001-344463-10521 awarded by the USDA. The Government has certain rights in the invention.

REFERENCE TO SEQUENCE LISTING, A TABLE, OR A COMPUTER PROGRAM LISTING COMPACT DISC APPENDIX

Not applicable.

TECHNICAL FIELD

This invention describes a method for synthesizing carbohydrate acids through controlled oxidation of their corresponding carbohydrates using nitric acid and oxygen as the oxidizing agents.

BACKGROUND OF THE INVENTION

Carbohydrate acids, and in particular carbohydrate diacids (aldaric acids) offer significant economic potential as carbon based chemical building blocks for the chemical industry, as safe additives or components of products use in pharmaceutical preparations and food products, and as structural components of biodegradable polymers, if they can be effectively produced on an industrial scale. Glucaric acid, for example, is produced through the oxidation of glucose and in salt form is currently in use as a nutraceutical for preventing cancer. The price of this material however is high, approximately $100/lb. Industrial scale production of aldaric acids would also provide sufficient materials for the production of other useful compounds, that include environmentally degradable polyamides with varying properties and applications, which are otherwise not commercially available.

Carbohydrate diacids are produced a number of ways from reducing sugars using a variety of oxidizing agents, nitric acid being among the earliest reported.[1] An example of a nitric acid oxidation of a carbohydrate is that of D-glucose to give D-glucaric acid, typically isolated as its mono potassium salt.[2,3,4] Alternatively, D-glucaric acid can be isolated from nitric acid oxidation of D-glucose as a disodium salt[5] or as the 1,4:6,3-dilactone.[6] Routes have been described showing synthesis of diacids through catalytic oxidation with oxygen over a noble metal catalyst.[7] An additional route of synthesis exists by use of oxoammonium salts in combination with hypohalites as the terminal oxidants. For example, Merbough and coworkers describe oxidation of D-glucose, D-mannose and D-galactose to their corresponding diacids using 4-acetylamino-2,2,4,6-tetamethyl-1-piperidinyloxy (4-AcNH-TEMPO) with hypohalites as the oxidizing medium.[8,9] A microbial oxidation of myo-inositol to glucuronic acid which is then oxidized enzymatically or by catalytic oxidation to glucaric acid has also been recently described.[10]

When used to oxidize carbohydrates to carbohydrate acids, nitric acid offers the advantages of conveniently serving as the solvent medium for the oxidation and as an oxidizing agent. However, there are also specific disadvantages. Such oxidation reactions can be very exothermic and may run away if care is not taken to control the exotherm in the early stages of the reaction. These reactions also generate significant amounts of NOX gases which are environmental hazards if they are vented into the atmosphere rather than being captured and rendered harmless and/or recycled in a process that regenerates nitric acid. Thus, it would be desirable to utilize a more controlled nitric acid oxidation process that does not run the burdensome, time consuming, and inefficient risk of overreaction, thereby rendering the products essentially useless, while at the same time employing a process that does not vent NOX gases into the atmosphere, and recycles these gases into nitric acid.

In the nitric acid oxidation of many compounds, product isolation can be encumbered by the residual nitric acid that remains in the usually syrupy product. Thus, in order to properly isolate the desired oxidation product, it is generally necessary to remove the residual nitric acid. This is particularly the case in the nitric acid oxidation of alcohol compounds, such as carbohydrates. In order to isolate the desired oxidation product of a carbohydrate, nitric acid must be at least partially removed. A number of methods have been described for removing residual nitric acid.

The first technique involves neutralizing aqueous nitric acid and organic/carbohydrate acids solution at the end of the oxidation step with hydroxide solution. In the case of D-glucose oxidation to obtain D-glucaric acid, potassium hydroxide is the base of choice and back titration with nitric acid yields the monopotassium salt of D-glucaric acid.[3,4] This technique is not advantageous due to the cost and difficulty involved in the neutralization step.

A second technique for removing residual nitric acid from the oxidation product involves repeated concentrations, by a distillation process, using additions of fresh quantities of water between each step,[2,6] after the bulk of the nitric acid has been removed by a distillation process of some type. Removal of residual nitric acid in this manner is very energy intensive requiring multiple additional distillations and does not efficiently remove all of the nitric acid.

Yet a third technique for removing residual nitric acid involves adding large volumes of 2-propanol in order to destroy any excess nitric acid.[11] The 2-propanol addition is followed by water dilution and concentration of the remaining product. This process further requires the consumption of 2-propanol, resulting in acetone and other residuals that must also be isolated and separated from the oxidation product. Further, this technique also describes treatment with water and hydrogen chloride, both of which must be removed from the oxidation product. This third technique involves too many steps to be economically viable.

As mentioned earlier, another disadvantage to nitric acid carbohydrate oxidation processes previously reported is the big exotherm normally associated with these oxidations. In those previous processes, the entire amount of solid carbohydrate, along with the entire amount of inorganic nitrite, which serves as a reaction activating agent, is mixed with the nitric acid at the outset of the reaction, thereby creating the conditions for a large and difficult to control exotherm that develops as the reaction warms. Alternatively, the solid carbohydrate is added portion-wise to the nitric acid. This process still promotes an extensive exothermic reaction and is also encumbered by the difficulty in adding solid carbohydrate portion-wise to the liquid/gaseous reaction mixture. Furthermore, isolation of the carbohydrate acid as a salt can also be made difficult due to the presence of inorganic nitrate which can contaminate carbohydrate acid salts during their isolation process.

Thus, significant industrial scale production of aldaric acids requires an economically efficient and a less complicated method for synthesizing aldaric acids from their corresponding carbohydrates. At this time, for example, D-glucaric is not manufactured on a significant industrial scale because there is no economically viable means for such production. The potential importance of D-glucaric acid as a chemical staple from renewable resources was recently underscored in a report by T. Werpy and G. Petersen.[12] From among hundreds of compounds considered as potential key chemical building blocks from renewable resources, glucaric acid was targeted as one of the top twelve molecules with significant potential as a chemical building block for a range of potential applications. Also included with glucaric acid were the structurally related pentaric acids, xylaric acid[11] from biomass xylose and arabinaric acid from biomass arabinose. The need for suitable oxidation methods of the precursor monosaccharides was emphasized by Werpy and Peterson. If a suitable economic means for the oxidation of carbohydrates could be found, the production of D-glucaric acid and other aldaric acids could see increased production, lower prices, and greater public availability.

All patents, patent applications, provisional patent applications and publications referred to or cited herein, are incorporated by reference in their entirety to the extent they are not inconsistent with the teachings of the specification.

BRIEF SUMMARY OF THE INVENTION

An improved method for oxidation of water soluble organic compounds subject to nitric acid oxidation, and particularly carbohydrates of different structures, stereochemistry, and origins, to their corresponding carbohydrate acids, including aldaric acids, addresses issues normally arising in common nitric acid oxidation methodologies. Specifically, the subject method serves to eliminate thermal control issues in the oxidation, the release of oxides of nitrogen into the atmosphere, but provides for removal of post-reaction nitric acid and inorganic compounds, while employing a catalytic process involving use of oxygen to carry out the desired oxidations. As a result, beneficial carbohydrate acids which were previously expensive and burdensome to produce can become relatively cheap and readily obtainable. Furthermore, many aldaric acids that were previously unavailable are now capable of industrial production and commercial development.

The first step of the subject method is the computer-controlled, catalytic oxidation reaction, wherein nitric acid is put in a closed reactor in contact with various carbohydrate feed-stocks under very mild and controlled conditions of oxygen pressure, reaction time, and reaction temperature to allow the oxidation of the carbohydrates to occur. Oxygen consumption in the presence of the aqueous acid solution is associated with nitric acid regeneration from various NOX gases as they are produced in the reaction. Carrying out this step in a controlled manner under relatively low temperature over time avoids the big exotherm normally associated with nitric acid oxidations. The next step in the process is to isolate the oxidized product by removing and recovering the bulk of the nitric acid by distillation, then treating the resulting product with inorganic hydroxide to a basic pH in order to neutralize any residual nitric acid and convert carbohydrate acids into their corresponding acid salts. The resulting aqueous solution, which contains inorganic nitrate and the salt(s) of the product carbohydrate acid(s), is subjected to a filtration leaving the retentate containing the organic acid(s) salt form(s) and the permeate containing the inorganic salts. At this stage, the absence of most of the nitric acid and/or inorganic nitrate from the retentate renders the ease of purification and isolation of the carbohydrate acid non-salt(s) product(s) much improved over previously reported methods. An additional method employed to separate nitric acid from product organic/carbohydrate acids is diffusion dialysis technology. This low energy process is typically employed to separate inorganic acids from metal salts,[13,14] particularly multivalent cation salts, but has not been applied extensively, or at all, to separation of inorganic acids from carbohydrates or carbohydrate acids. The nitric acid recovery stream and organic/carbohydrate acids products streams can be separately processed for nitric acid reuse and organic/carbohydrate acids salts isolation, respectively. Diffusion dialysis separation of nitric acid from organic/carbohydrate acid products offers the additional option of being applied to the oxidation mixture before or after evaporative removal of some portion of the nitric acid, depending upon the advantage that can be utilized on an industrial scale. As with the filtration technology, application of the diffusion dialysis technology ultimately improves product isolation.

DETAILED DESCRIPTION OF THE INVENTION

The process of the subject invention is a convenient, simple and general catalytic oxidation process for converting available carbohydrates into their various corresponding acids.

The first step of the subject method is the controlled oxidation of various carbohydrate feed-stocks with nitric acid. The oxidation reaction is accomplished by charging a reactor with nitric acid, in the molar ratio range of 2:1 to 10:1, nitric acid to starting monosaccharide(s) and/or monosaccharide(s) units as found in di-, oligo- and/or polysaccharide(s). Continuous monitoring and control of reaction temperature, pressure, and stirring rate, plus introduction of gases and addition of liquids and/or solutions to the reaction is computer controlled. The reactor is then put under a positive pressure of oxygen and an aqueous solution of the carbohydrate is pumped into the nitric acid at a chosen programmed rate. The typical large exotherm associated with nitric acid oxidations of carbohydrates is avoided by carrying out the addition of the aqueous carbohydrate solution at a relatively low temperature, typically 20-30° C., while the reaction mixture is under positive pressure of oxygen. Nitric acid oxidation temperatures of 44-48° C. were previously reported for oxidation of D-glucose and D-xylose when the reaction mixture was cooled by the bubbling oxygen or nitrogen gas through the reaction mixtures.[5] However, the latter oxidations were not carried out under an atmosphere of oxygen in a closed reactor, and the gases were employed to cool the reaction mixture. Employing the improved method, the reaction temperatures required are significantly lower than the typical temperatures of 55-65° C. reported for the oxidation of D-glucose.[2-5] Concurrently, multiple, small measured amounts of inorganic nitrite, such as sodium or potassium nitrite, in aqueous solution are added over time, to the reaction mixture within the closed reactor according to a programmed recipe. The addition of aqueous inorganic nitrite in such a manner provides for continued reaction activation during the entire addition period of the aqueous carbohydrate solution, as opposed to a short and less effective activation protocol wherein several small portions of solid inorganic nitrite were added over a brief (20 minutes) period of time as previously reported.[4] Once the above-mentioned additions are complete, the reaction temperature can be maintained or changed in a controlled manner, typically to a slightly higher temperature, while at the same time oxygen pressure can be programmatically maintained or changed to a desired level. Both reaction temperature and pressure can be controlled for as long as desired. Typically, the entire oxidation process is carried out in under 8 hours.

Also produced in the oxidation are gaseous oxides of nitrogen (NOX gases), dominated by nitrogen dioxide and nitric oxide which are recycled to nitric acid in an aqueous/oxygen environment.[15] Other NOX gases, such as nitrous oxide, require additional abatement processing. Existing technologies are employed in industrial nitric acid oxidations, notably nitric acid oxidation of cyclohexanol/cyclohexanone to adipic acid, that abate most of the oxides of nitrogen from those processes[16] and can be applied to the applicants' invention described here.

This reaction can be described as a catalytic oxygenation process wherein nitric acid serves as the direct source of the actual oxidizing species, but is regenerated in part through the use of oxygen that is consumed during the course of the reaction, and which serves as an oxidizing agent for conversion of low oxidation state NOX gases to higher nitrogen oxidation state NOX gases, e.g,. NO to $NO_2$.[15] Added oxygen may play additional positive roles in the oxidation mechanism but those roles are not clearly determined at this time. However, the use of oxygen in the reaction as indicated allows the oxidation to proceed at relatively low temperature, typically 25-40° C. for hexoses, such as D-glucose and D-mannose, and somewhat higher temperatures for pentoses, such as D-xylose. The higher oxidation temperature required for pentoses may result from the difference in reactivity of the terminal primary hydroxyl groups compared to those of the hexoses. When a pentopyranose or hexopyranose ring form (predominant forms of pentoses and hexoses in aqueous solution) is oxidized, the dominant first site of oxidation is at the anomeric hydroxyl group, generating the corresponding six-membered, 1,5-aldono lactone. The terminal (C-6) hydroxyl group on hexose-derived aldono lactones is directly available for oxidation to a carboxylic acid function, whereas the terminal (C-5) hydroxyl group on pentose-derived aldono lactones is tied up in the lactone ring and is only available for oxidation upon hydrolysis of the lactone to the acyclic aldonic acid structure. Thus, oxidation of the terminal hydroxyl group of the pentose-derived aldonic acid is found to require a higher reaction temperature, presumably in order to facilitate the necessary hydrolysis of the lactone in the aqueous acid medium, to generate the ring open aldonic acid with a terminal hydroxyl group that is now available for the second oxidation to occur.

Employing the computer controlled process as described also significantly allows for improved opportunities for selective oxidations. As illustrated with the pentoses, the first oxidation step produces predominantly the monocarboxylic acid lactone (aldono lactone), which under the reaction conditions can be in equilibrium with the open chain aldonic acid. The same type of selectivity is observed with the hexoses and aldoses in general, an aldonic acid is formed first by oxidation at aldehyde/anomeric carbon, followed by further oxidation at a second site, primarily at the terminal hydroxyl group, but not limited to the terminal hydroxyl group. In general, the second oxidation on a carbohydrate substrate typically requires more severe reaction conditions than are required for the first oxidation, e.g., longer reaction time, increased temperature, additional nitric acid, etc., to accomplish the oxidation. The reaction rates for the first oxidation and for additional oxidation reactions vary depending upon which carbohydrate is being oxidized. Consequently, use of a computer controlled reaction process, allows for ready selection of reaction parameters that can be applied to specifically produce as a dominant product, a single oxidation product, a double oxidation product, etc., or a mixture of carbohydrate derived oxidation products that may have added value because they perform in an application as required but don't require added processing and expense needed for isolation of a single oxidation product, from carbohydrates of various classes (aldoses, ketoses, di- and larger saccharides, aldonic acids, alduronic acids, alditols, etc.).

The reaction parameter control and convenience that comes with the application of this technology makes it possible to carry out selective oxidations on a range of organic compounds subject to nitric acid oxidation, to make a range of oxidized products.

Organic compounds subject to nitric acid oxidation useful in the subject method include alcohols, aldehydes, ketones, and carbohydrates. Carbohydrates useful in the subject method include, but are not limited to, monosaccharides, such as the common monosaccharides D-glucose, D-mannose, D-xylose, L-arabinose, D-arabinose, D-galactose, D-arabinose, D-ribose, D-fructose; disaccharides, such as the common disaccharides maltose, sucrose, isomaltose, and lactose; oligosaccharides, for example, maltotriose and maltotetrose; aldonic acids such as D-gluconic acid, D-ribonic acid, and D-galactonic acid; aldonic acid esters, lactones and salts that include but are not limited to those derived from D-gluconic acid, D-ribonic acid and D-galactonic acid; alduronic acids, for example, D-glucuronic acid and L-iduronic acid; alduronic esters, lactones and salts that include but are not limited to those derived from D-glucuronic acid and L-iduronic acid; alditols that include glycerol, threitol, erythritol, xylitol, D-glucitol; alditols with more than six carbon atoms; cyclitols, for example common cyclitols such as myo-inositol and scyllitol; corn syrups with different dextrose equivalent values; mixtures of carbohydrates from different biomass, plant or microorganism sources; polysaccharides from biomass, plant or microorganism sources and of varying structures, saccharide units and molecular weights.

Suitable inorganic nitrites for use in the subject method include but are not limited to ammonium nitrite, sodium nitrite, potassium nitrite, lithium nitrite and any available nitrite salt.

In order to isolate the target aldaric acids, the bulk of the nitric acid is first removed from the reaction mixture. Two methods for separating the nitric acid from the organic product(s) are: 1) evaporation or distillation of the nitric acid, often under reduced pressure; 2) diffusion dialysis. The bulk of the product(s) composition from nitric acid oxidation of carbohydrates are organic acids comprised of primarily carbohydrate acids and to a small extent, non-carbohydrate acids such as glycolic acid and oxalic acid. All of these acid products will be simply designated hereafter as organic acids or organic acid(s) products. In reported oxidations, in order to isolate the target aldaric acids, the solvent/reagent nitric acid is either converted to inorganic nitrate with base (e.g., potassium hydroxide[3,4]) and/or removed by an evaporation process.[2,6,11] Neutralization to a pH>7 with inorganic base, without removal of nitric acid, requires base for all of the nitric acid plus the organic/carbohydrate acid(s) and the nitric acid is not directly recovered for further use. In contrast, partial recovery of the nitric acid for reuse by vacuum distillation is advantageous because the recovered nitric acid can be used again for oxidation purposes, although it is difficult to remove all the residual nitric acid from the syrupy residue with ease. The second method for nitric acid recovery is through the use of diffusion dialysis. This process is typically used for the separation of common inorganic acids such as hydrochloric acid, sulfuric acid, or nitric acid from multivalent metal cations such as $Cu^{++}$ or $Z^{++}$[13,14] The aqueous acid feedstock of the inorganic acid and metal salt(s) and a separate water stream are routed through a diffusion dialysis system consisting of low pressure pumps and an appropriate membrane system. Two aqueous exit streams are generated, an acid recovery stream comprised primarily of inorganic acid with some metal salt(s), and a product recovery stream comprised of primarily metal salt(s) with some inorganic acid. The separate streams can be subjected to further diffusion dialysis as needed to give a stream with higher inorganic acid concentration and lower metal salt(s) concentrations, and a stream with higher metal salt(s) concentration and lower inorganic acid concentration. This separation technique was applied to nitric acid oxidation reaction mixtures as prepared by the described methods herein, and was found to perform in the same manner as used in separation of inorganic acid(s) from metal salt(s). The bulk of the nitric acid with some organic acid(s) product(s), was in the acid recovery stream, and the bulk of the organic acid(s) product(s) with some of the nitric acid, was in the organic product recovery stream. The use of this technology to separate nitric acid from the organic acid(s) product(s) produced from the oxidation process described here is a very low energy process, operates at ambient temperature, and can be run continuously. It offers an additional advantage over direct evaporation/distillation of nitric acid from the reaction mixture in that in the latter process, additional oxidative processes can occur generating additional NOX gases that have to be contained, removed and/or converted to oxides of nitrogen that are convertible to nitric acid. In contrast, the recovered nitric acid from the diffusion dialysis process is low in carbohydrate product content and evaporation/distillation of the recovered nitric acid is achieved with minimal oxidation and NOX formation occurring during nitric acid recovery.

Depending upon the starting carbohydrate(s), the specific reaction conditions employed, and the target product(s) this solution can be treated accordingly to give the carbohydrate acid(s) in one or more forms. Aldaric acids can be obtained in free acid forms, as disalts, mono salts, acid lactones, and/or dilactones, or as mixtures of various salt forms, and/or acid and/or acid lactone forms. Aldonic acids can be isolated as their free acid forms, and/or lactones, and/or mixtures of salts. Acids generated from oligosaccharides and other higher molecular weight carbohydrates are mixtures which can contain some of the above aldonic and aldaric acids plus higher molecular weight acids derived from higher molecular weight carbohydrates. These acids can be also be obtained in various acid, lactone and salt forms.

The presence of residual nitric acid in the syrupy product makes it difficult to isolate an acid form or lactone form of the target carbohydrate acid(s). It was recently demonstrated that improved isolation of the dilactone form of both D-glucaric and D-mannaric acid[6] was possible, but only after more complete removal of residual nitric acid by extraction with an ether followed and drying under high vacuum.[6] When oxidation product(s) is (are) obtained from direct concentration of the reaction mixture that removes most of the nitric acid, or by subjecting the oxidation reaction mixture to diffusion dialysis followed by removal of the bulk of the remaining nitric acid by an evaporation/distillation step, residual nitric acid can be removed as nitrate and recovered by a membrane filtration method. When the resultant syrupy product/residual nitric acid mixture is treated with inorganic hydroxide to a pH>7, the resulting solution contains inorganic nitrate and the salt(s) of the product organic acid(s). This solution is then subjected to filtration, typically nanofiltration, with the bulk of inorganic nitrate passing through the membrane and into the permeate, and the bulk of the organic product remaining in the retentate. Removal of inorganic nitrate from carbohydrate acid salts after nitric acid oxidation was previously reported using ion retardation chromatography.[5] However, that method is not as fast, not as applicable on a large scale, and not as efficient as the filtration method described here. In the instant process, the remaining retentate contains the organic acid(s) salt form(s) with no to low inorganic salt content. The presence of only small amounts of inorganic nitrate in the organic acid(s) salts product(s) renders purification and/or isolation of the aldaric acid salt(s) product(s) or non-salt product(s) much improved over previously reported methods.

Overall, the use of a computer controlled reaction process, adding the carbohydrate and inorganic nitrite to the nitric acid in aqueous solution, and carrying out the oxidation in a closed reactor under a positive pressure of oxygen allows oxidations of carbohydrates with nitric acid to be carried out under very mild conditions in a catalytic fashion. Isolation and purification of the carbohydrate acid(s) and/or salt form(s) is considerably improved by removing the bulk of nitric acid by distillation under reduced pressure and/or separating the nitric acid from the carbohydrate acid(s) by diffusion dialysis and then recovering nitric acid using an evaporation/distillation process. Thereafter, neutralization of residual nitric acid and organic acid(s) product(s) with inorganic hydroxide can be followed by separation of residual inorganic nitrate from organic acid(s) salt(s) using filtration technology.

The following examples are offered to further illustrate but not limit both the compositions and the methods of the present invention. All percentages are by weight and all solvent mixture proportions are by volume unless otherwise noted.

EXAMPLE 1

General Methods

Solutions were concentrated in vacuo (10-15 mbar) using a rotary evaporator and water bath at 50° C. pH measurements were made with a Thermo Orion 310 pH meter (Thermo Fisher Scientific, Inc., Waltham, Mass., USA) which was calibrated prior to use. Oxidations were carried out in Mettler Toledo Labmax reactor. The Labmax reactor is designed to operate as a computer controlled closed-system reactor. The Labmax was fitted with a top-loading balance, a liquid feed pump, an oxygen Sierra flow valve, a mechanically driven stirring rod, a thermometer, a 1 liter thermal jacketed flask, a FTS recirculating chiller, a pressure manifold fitted with pressure relief valves and pressure gauge and a personal computer with CamileTG v1.2 software. The software installed allows the operator to program experiments based on specific parameters and conditions.

EXAMPLE 2

Nitric Acid Oxidation of D-glucose

The aqueous 62.3% D-glucose solution used in the oxidations was prepared by adding solid D-glucose (162.5 g, 0.75 mol) to 97.5 grams of deionized water in a screw-capped flask containing a stir bar. Prior to adding solid D-glucose to the water, the water was heated to ca. 60° C. with stirring. Once the D-glucose was dissolved, the temperature was reduced to ambient and dry sodium nitrite (0.60 g) added to the solution. The total weight of the solution is 260.6 g.

The Recipe Menu is accessed using the Labmax CamileTG v1.2 software and the reaction parameters for the oxidation were programmed in a series of stages: Stage 1—the reactor temperature was set at 25° C.; the stirring rod speed set at 200 rpm (and held constant throughout all the remaining stages); time set for 1 minute. Stage 2—the reactor temperature was set at 25° C., and the pressure set at 0.25 bar for a duration of 3 minutes. Stage 3—the temperature of the reactor was set at 25° C., the pressure at 0.25 bar, and 43.3 grams of a 62.3% (w/w) D-glucose solution, containing 0.23% by weight of sodium nitrite, set to be added over 30 minutes. Stage 4—the reactor temperature was set at 25° C., the pressure maintained at 0.25 bar, and the duration of the stage set to 10 minutes. Stage 5—the reactor temperature was set at 25° C., the pressure at 0.25 bar, and 172.9 grams of the 62.3% (w/w) D-glucose solution, containing 0.23% by weight of sodium nitrite, set to be added over a 90 minute period. Stage 6—a 5 minute stabilization period was set where the temperature remains at 25° C. and the pressure at 0.25 bar. Stage 7—the temperature of the reactor was set to rise to 30° C. and the pressure set to increase to 0.50 bar over 60 minutes. Stage 8 was set for a duration of 180 minutes, the temperature and pressure set to remain constant at 30° C. and 0.50 bar, respectively. Stage 9—the reactor temperature was set to cool to 25° C. over 10 minutes. Once the reaction has been programmed to proceed as indicated, nitric acid (68-70%, 187 mL, ca. 3.0 mol) was added to the reactor. The reaction recipe was initiated and starting at stage 1, the reactor was closed to the atmosphere. In addition to activating the reaction recipe the hardware components of the reactor were also activated. Those hardware components include a top-loading balance, a liquid feed pump, pressure sensor, thermometer, oxygen Sierra flow valve, an FTS recirculating chiller and oxygen canister with a pressure regulator preset at 38.5 psi.

When the reaction had progressed through all of the stages, the reaction mixture was cooled to room temperature and then removed from the reactor through the bottom valve of the reactor.

The reaction mixture can then be worked up using different procedures. In one procedure the reaction mixture was concentrated at reduced pressure (rotary evaporator) with adequate cooling. The first fraction distilled at ca. 23-34° C. and 50-120 millibar of pressure and appeared to be NOX gases as evidenced from the brown color of nitrogen dioxide gas. The liquid distillate fractions distilled between 26-43 millibars and 26-39° C. and have specific gravities that increase from 1.05 to 1.25, in keeping with the negative azeotropic character of nitric acid. In a second procedure, separation of nitric acid from organic product was carried out employing diffusion dialysis. The Mech-Chem Diffusion Dialysis Acid Purification System laboratory scale Model AP-L05 was used to separate nitric acid from the organic product. The Mech-Chem system contains two metering pumps, the first being the acid reclaim pump and the second being the acid reject pump. Oxidation of D-glucose as described above was repeated five times, each reaction mixture was diluted with reverse osmosis (RO) filtered water to a volume of 1000 mL. The organic product concentration was estimated to be about 0.75 molar, and the nitric acid concentration estimated to be about 3.0 molar. The acid reject pump was set at 30% (pump length) and 30% (pump speed) and the acid reclaim pump was set at 40% (pump length) and 40% (pump speed). This put the reclaim to acid reject ratio at about 1.2. The system was first primed with RO water according to a standard setup procedure and then the water was removed from the acid tank in the unit. The acid tank was then filled with the diluted aqueous oxidation mixture and the water tank in the unit was filled with RO water. The acid purification unit was turned on with the pumps set as indicated and the process was initiated. Over a period of some 74 hours of processing, the entire oxidation mixture solution (approximately 5 liters) was added to the acid feed tank, RO water added to water feed tank, and the acid recovery stream and product recovery streams were collected. Samples were taken periodically and analyzed using a Dionex ICS-2000 Ion Chromatography (IC) System. Concentrations of components of samples taken from the acid recovery stream and product recovery stream were reported in parts-per-million. Analysis of the IC data showed that >90% of the nitric acid was in the acid recovery stream along with 30% of the organic product. The product recovery stream contained <10% of the nitric acid and 70% of the organic product. The nitric acid from the nitric acid stream was recovered by a standard distillation process and the organic product from the product reclaim stream recovered by basification as described, then used directly or subjected to the nanofiltration procedure as needed to further remove inorganic nitrate.

Isolation of glucaric acid as its disodium salt.[5] D-Glucose (162.5 g, 0.75 mol) was oxidized using the LabMax reactor as described. Following the completion of the reaction, the reaction solution was concentrated to a white foam in vacuo (10-15 mbar) using a rotary evaporator and water bath at 50° C. The concentrate of organic product(s) and residual nitric acid was diluted with deionized water (150 mL), titrated with sodium hydroxide solution (5 M) to an approximate pH of 9.5, and then diluted with deionized water (3700 mL), giving an approximate 2.5% (w/w) solids solution. This solution was then filtered using a nanofiltration unit. The nanofiltration unit, built in-house, is comprised of the necessary valves, pump, lines, pressure gauge and an appropriate membrane such as a GE DL2540F membrane. When the permeate volume reached 1000 mL, 1000 mL of reverse osmosis (RO) purified water was added to the feedstock. The typical rate of the permeate flow when reducing the volume by 1000 mL was 48 mL/min. When 2000 mL of permeate was removed, another 1000 mL of RO water was added to the feedstock. The typical rate of permeate flow when removing the second 1000 mL was 45 mL/min. This procedure was repeated until a total of 4000 mL had been removed via the permeate and 4000 mL of RO water had been added to the feedstock. The typical permeate flow rate when removing the last 1000 mL was 43 mL/min. The filtration process was continued after the last 1000 mL of RO water was added to the feedstock until the permeate flow slowed to a trickle at which time the filtration was stopped. The final volumes of the retentate and permeate were 2800 mL and 5200 mL, respectively. Analysis of the permeate and retentate by ion chromatography (IC) indicated that sodium nitrate is the major component of the permeate and is present only in minor amounts in the retentate. The retentate was concentrated under reduced pressure using a rotary evaporator and further dried in a vacuum oven to yield crude disodium D-glucarate (186.52 g, 97.9% based on pure disodium D-glucarate). The salt was then dissolved in water, and the pH of the solution adjusted with sodium hydroxide to pH 8. The product was precipitated with methanol (1000 mL) as an off white solid (146.24 g, 76.7% based on pure disodium D-glucarate).

EXAMPLE 3

Nitric Acid Oxidation of D-glucose

The oxidation of D-glucose was carried out as in Examples 1 and 2. However, potassium hydroxide was substituted for sodium hydroxide in the neutralization process to give crude D-glucaric acid dipotassium salt (151.25 g, 70.4% based on pure dipotassium D-glucarate). The salt was precipitated from methanol as described to give an off white solid (145.75 g, 67.9% based on pure dipotassium D-glucarate).

Monopotassium D-glucarate isolation, Method 1. D-Glucose (162.5 g, 0.75 mol) was oxidized using the LabMax reactor and concentrated as described. The concentrate of organic product(s) and residual nitric acid was diluted with deionized water (150 mL) and chilled at 5° C. for 18 h. The pH of the solution was adjusted to a constant pH of 9.1 with 45% KOH (184 mL) in an ice bath and the solution back-titrated to pH 3.4 with concentrated $HNO_3$ (34.6 mL) in an ice bath. A precipitate formed when the solution pH dropped below 5. After cooling the mixture at 5° C. for 4 h, the precipitate was isolated by filtration. The off-white solid was returned to a beaker and triturated in water (200 mL) at 50° C. for 30 min then cooled to 5° C. for 1 h before isolating the solid by filtration. The solid was washed with cold water (20 mL) and dried in a vacuum oven to yield monopotassium D-glucarate[2-5] as a white solid (86.2 g, 0.347 mol, 46.3%).

Monopotassium D-glucarate isolation, Method 2. D-Glucose (162.5 g, 0.75 mol) was oxidized using the LabMax reactor and concentrated as described. The concentrate of organic product(s) and residual nitric acid was diluted with deionized water (500 mL) and chilled at 5° C. for 18 h. The pH of the solution was adjusted to a constant pH of 9.5 with 10% KOH (1.1 L) in an ice bath. The resulting brown solution was diluted to 4 L and processed using a nanofiltration procedure (e.g., a GE DL2540F membrane) as described. The pH of the retentate from the filtration was raised from 8 to 10 with 10% KOH (15 mL), the retentate concentrated using a rotary evaporator to a volume of 300 mL, and the solution pH adjusted to 3.4 with concentrated HCl (46.2 mL) in an ice bath. A precipitate formed when the solution pH dropped below 5. After cooling the mixture at 5° C. for 4 h, the precipitate was isolated by filtration. The off-white solid was returned to a beaker and triturated with cold water (200 mL) for 30 min. The solid was isolated by filtration, washed with cold water (20 mL), and dried in a vacuum oven to yield monopotassium D-glucarate as a white solid (87.4 g, 0.352 mol, 46.9%).

EXAMPLE 4

Nitric Acid Oxidation of D-gluconic Acid δ-lactone

The oxidation of D-gluconic acid δ-lactone was carried out as in Examples 1 and 2 with changes as noted in Stages 3 and 5 (Example 2). Stage 3—the temperature of the reactor was set at 25° C., the pressure at 0.25 bar, and 43.3 grams of a 62.3% (w/w) D-gluconic acid δ lactone solution, containing 0.23% by weight of sodium nitrite, were set to be added over 30 minutes. Stage 5—the reactor temperature was set at 25° C., the pressure at 0.25 bar, and 170.5 grams of the 62.3% (w/w), D-gluconic acid δ-lactone containing 0.23% by weight of sodium nitrite, added over a 90 minute period. Product isolation can be carried out by any of the methods previously described.

EXAMPLE 5

Nitric Acid Oxidation of D-mannose

Oxidation of D-mannose was carried out using the Mettler Toledo RC-1 Labmax reactor as described in Examples 1 and 2 (D-glucose) with the following changes: The reactor was charged with the following 5.0 mol of nitric acid (312.5 mL, 68-70%). Stage 3—62.5% D-mannose solution (43.3 g) was added in place of D-glucose. Stage 5, 62.5% D-mannose solution (173.9 g) was added in place of D-glucose. In Stages 1-6 of the reaction the temperature was maintained at 30° C. and 0.25 bar. In Stage 7 the temperature was raised to 40° C., and maintained at that temperature through Stage 8, 6 h. Stage 9 remained unchanged.

Isolation of D-mannaric acid as its disodium salt. Prior to titration with sodium hydroxide the solution was stirred at 60° C. for approximately 45 min to promote equilibration between D-mannaric acid acid and lactone species. The isolation procedure was then followed as in Example 1 to give crude mannaric acid disodium salt: 144.4 grams (92% based on pure disodium D-mannarate).

EXAMPLE 6

Nitric Acid Oxidation of D-xylose

The procedure described in Examples 1 and 2 for D-glucose was applied to D-xylose using the same molar amount of starting D-xylose (112.52 g, 0.749 mol) and same amount of sodium nitrite (0.83 g). The differences in the stages for the oxidation process are as follows: addition stages 3 and 5 were combined [181.14 g of a 62.5% (w/w) D-xylose solution containing 0.46% by weight of sodium nitrite were added over 120 min], stage 4 was eliminated. The next change is in new stage 6 (glucose oxidation stage 7) wherein the temperature was raised to 35° C. and the pressure raised from 0.25 bar to 0.50 bar in 60 min. New stage 7 (glucose oxidation stage 8) reaction time increased from 180 to 210 min. New stage 8 is the same as glucose oxidation stage 9. After concentrating the reaction mixture, the resulting syrup was diluted with water (300 mL) and titrated with NaOH (5.0 M) to pH 3.5 to give an insoluble side product, disodium tetrahydroxybutanedioate acid[17] (8.39 g, 37.1 mmol, 4.95% yield) isolated by filtration. The filtrate was then further treated with sodium hydroxide to pH 8.5 and subjected to the filtration process as in Example 1. The aqueous retentate was concentrated to the solid crude disodium salt product (140.2 g, 624.7 mmol, 83.3% yield, based on pure disodium xylarate).

Example 7

Nitric Acid Oxidation of L-Arabinose

The procedure described in Examples 1 and 2 for D-glucose was applied to L-arabinose using the same molar amount of starting L-arabinose (113.31 g, 0.754 mol) but an increased amount of nitric acid (320 mL, 5.31 mol). The differences in the stages for the oxidation process are as follows: addition stages 3 and 5 were combined [226.62 g of a 50% (w/w) L-arabinose solution containing 0.77% by weight of sodium nitrite are added over 90 min], stage 4 was eliminated. In new stage 6 (glucose oxidation stage 7) the temperature was raised to 50° C. and the pressure raised from 0.25 bar to 0.50 bar in 45 min. New stage 7 (glucose oxidation stage 8) reaction time increased from 180 to 240 min. New stage 8 is the same protocol as glucose oxidation stage 9. The oxidation mixture was then concentrated under reduced pressure as described in the glucose oxidation, yielding a thick syrup. The syrup was dissolved in 200 mL DI water and titrated with 5M NaOH to pH 3.5 . A precipitate (disodium tetrahydroxybutanedioate,[17] 4.26 g, 18.9 mmol, 2.5% yield) was removed by filtration. The resulting solution was then titrated with 5M NaOH, to pH 8.5 , diluted to 3 L with DI water and processed using the nanofiltration separation protocol. The resulting retentate was concentrated under reduced pressure and further dried overnight in a vacuum oven at 50° C. to yield crude disodium L-arabinarate (125.1 g, 558.2 mmol, 74.4% yield based on pure disodium L-arabinarate). The crude disodium L-arabinarate was triturated with ethanol (300 mL), separated by filtration, and dried under vacuum; yield 73.5%.

It is understood that the foregoing examples are merely illustrative of the present invention. Certain modifications of the articles and/or methods may be made and still achieve the objectives of the invention. Such modifications are contemplated as within the scope of the claimed invention.

References

1 . J. Stanek, M. Cerny, J. Kocourek and J. Pacak, "The Monosaccharides,"Academic Press, New York and London, 1963 , p 741-752 , and references therein.
2 . W. N. Haworth and W. G. M. Jones, *J. Chem. Soc.*, 65-76 (1944); b.
3 . C. L. Mehltretter and C. E. Rist, *Agric. and Food Chem.*, 1, 779-783 (1953)
4 . C. L. Mehltretter, [14] "D-Glucaric Acid", in Methods in Carbohydrate Chemistry, R. L. Whistler, M. L. Wolfrom, Eds; Academic Press, New York, 1962 , Vol. II, pp 46-48.
5 . D. E. Kiely, A. Carter and D. P. Shrout, U.S. Pat. No. 5,599,977 , Feb. 4, 1997.
6 . D. E. Kiely and G. Ponder, U.S. Pat. No. 6,049,004 , Apr. 11, 2000.
7 . C. L. Mehltretter, U.S. Pat. No. 2,472,168 , Jun. 7, 1949.
8 . N. Merbough, J. M. Bobbitt and C. Bruckner, *J. Carbohydr. Chem.*, 21, 66-77 (2002).
9 . N. Merbouh, J. M. Bobbitt, and C. Bruckner, U.S. Pat. No. 6,498,269 , Dec. 24, 2002.
10 . W. A. Schroeder, P. M. Hicks, S. McFarlan, and T. W. Abraham, U.S. Patent Application, 20040185562 , Sep. 24, 2004).
11 . C. E. Cantrell, D. E. Kiely, G. J. Abruscato and J. M. Riordan, J. Org. Chem., 42, 3562-3567 (1977).
12 . T. Werpy and G. Petersen (Eds.) Top Value Added Chemicals from Biomass, Vol 1 Results of Screening for Potential; http:/www.osti.gov/bridge or U.S. Department Of Energy, Office of Scientific and Technical Information, P.O. Box 62 , Oak Ridge, Tenn. 37831-0062.
13 . D. E. Bailey, U.S. Pat. No. 5,264,123 , Nov. 23, 1993.
14 . D. R. Olsen and D. E. Bailey, U.S. Pat. No. 5,562,828 , Oct. 8, 1996.
15. "Advanced Inorganic Chemistry", F. A. Cotton and G. Wilkinson, $5^{th}$ ed., John Wiley, pp 341-353 , New York (1988).
16 . Heike Mainhardt, "$N_2O$ Emissions from Adipic Acid and Nitric Acid Production," in IPCC Good Practice Guidance and Uncertainty Management in National Greenhouse Gas Inventories, Jun. 15, 2001 , and references therein.
17 . A. Lachman, J. Amer. Chem. Soc., 43, 2091-2097 (1921).

The invention claimed is:

1. A mixture of organic acids and nitric acid prepared by a method comprising the steps of:
preparing an aqueous solution of an organic compound, wherein the organic compound is selected from the group consisting of monohydric alcohols, diols, polyols, carbohydrates, and mixtures of carbohydrates;
combining, over time, employing a controlled process, in a closed reaction vessel, under a positive pressure of oxygen, the aqueous solution of the organic compound and an aqueous solution of nitric acid to oxidize the organic compound to a mixture of organic acids;
maintaining controlled, moderate temperatures of from about 25° C. to about 50° C., controlled positive pressure of oxygen, and controlled agitation of the organic compound and nitric acid reaction mixture during the oxidation reaction; and
removing a portion of the nitric acid from the combined aqueous solution to give a mixture of organic acids.

2. The mixture of claim 1, wherein said method further comprises the step of making basic the solution from which a portion of nitric acid has been removed to convert residual nitric acid to inorganic nitrate and the mixture of organic acids to a mixture of organic acid salts.

3. The mixture of claim 1, wherein said aqueous solution of the organic compound is added to said aqueous solution of nitric acid.

4. The mixture of claim 1, wherein said aqueous solution of nitric acid is added to said aqueous solution of the organic compound.

5. The mixture of claim 2, wherein said solution from which a portion of nitric acid has been removed is made basic using an inorganic base selected from the group consisting of sodium hydroxide, potassium hydroxide, lithium hydroxide, ammonium hydroxide, sodium carbonate, potassium carbonate, and lithium carbonate.

6. The mixture of claim 1, wherein said controlled process of combining the solution of nitric acid and said aqueous solution of the organic compound is an automated process.

7. The mixture of claim 6, wherein said automated process is a computer controlled process.

8. The mixture of claim 1, wherein said temperature is controlled by an automated process.

9. The mixture of claim 8, wherein said automated process is a computer controlled process.

10. The mixture of claim 1, wherein said agitation is controlled by an automated process.

11. The mixture of claim 10, wherein said automated process is a computer controlled process.

12. The mixture of claim 1, wherein said positive oxygen pressure is controlled by an automated process.

13. The mixture of claim 12, wherein said automated process is a computer controlled process.

14. The mixture of claim 1, wherein said method further comprises combining an aqueous solution of an inorganic nitrite when combining said aqueous solution of nitric acid and said aqueous solution of an organic compound.

15. The mixture of claim 14, wherein said aqueous solution of nitric acid, said aqueous solution of the organic compound, and said aqueous solution of an inorganic nitrite are combined using a controlled process.

16. The mixture of claim 15, wherein said controlled process of combining the said solution of nitric acid, said aqueous solution of the organic compound, and said aqueous solution of an inorganic nitrite is an automated process.

17. The mixture of claim 16, wherein said automated process is a computer controlled process.

18. The mixture of claim 14, wherein said inorganic nitrite is selected from the group consisting of ammonium nitrite, sodium nitrite, potassium nitrite, lithium nitrite, calcium nitrite, or magnesium nitrite.

19. The mixture of claim 1, wherein said carbohydrates are selected from the group consisting of monosaccharides, disaccharides, oligosaccharides, aldonic acids, aldonic acid esters, aldonic acid lactones, aldonic acid salts, alduronic acids, alduronic acid esters, alduronic acid salts, alditols, cyclitols, corn syrups with different dextrose equivalent values, and monosaccharides, disaccharides, oligosaccharides, and polysaccharides derived from plant, microorganism, or biomass sources.

20. The mixture of claim 1, wherein said removing a portion of the nitric acid from the combined aqueous solution is accomplished by diffusion dialysis.

21. The mixture of claim 1, wherein said removing a portion of the nitric acid from the combined aqueous solution is accomplished by an evaporation/distillation process.

22. The mixture of claim 21, wherein said evaporation/distillation process is carried out under reduced pressure.

23. A mixture of organic acid salts and nitric acid prepared by a method comprising the steps of:
preparing an aqueous solution of an organic compound, wherein the organic compound is selected from the group consisting of monohydric alcohols, diols, polyols, carbohydrates, and mixtures of carbohydrates;
combining, over time, employing a controlled process, in a closed reaction vessel, under a positive pressure of oxygen, the aqueous solution of the organic compound and an aqueous solution of nitric acid to oxidize the organic compound to a mixture of organic acids;
maintaining controlled, moderate temperatures of from about 25° C. to about 50° C., controlled positive pressure of oxygen, and controlled agitation of the organic compound and nitric acid reaction mixture during the oxidation reaction;
making basic the reaction solution to convert residual nitric acid to inorganic nitrate and the mixture of organic acids to a mixture of organic acid salts; and
removing a portion of the inorganic nitrate from the combined aqueous solution to give a mixture of organic acid salts.

24. The mixture of claim 23, wherein said portion of the inorganic nitrate is removed by membrane filtration.

25. The mixture of claim 23, wherein said aqueous solution of the organic compound is added to said aqueous solution of nitric acid.

26. The mixture of claim 23, wherein said aqueous solution of nitric acid is added to said aqueous solution of the organic compound.

27. The mixture of claim 23, wherein said solution is made basic using an inorganic base selected from the group consisting of sodium hydroxide, potassium hydroxide, lithium hydroxide, ammonium hydroxide, sodium carbonate, potassium carbonate, and lithium carbonate.

28. The mixture of claim 23, wherein said controlled process of combining the solution of nitric acid and said aqueous solution of the organic compound is an automated process.

29. The mixture of claim 28, wherein said automated process is a computer controlled process.

30. The mixture of claim 23, wherein said temperature is controlled by an automated process.

31. The mixture of claim 30, wherein said automated process is a computer controlled process.

32. The mixture of claim 23, wherein said agitation is controlled by an automated process.

33. The mixture of claim 32, wherein said automated process is a computer controlled process.

34. The mixture of claim 23, wherein said positive oxygen pressure is controlled by an automated process.

35. The mixture of claim 34, wherein said automated process is a computer controlled process.

36. The mixture of claim 23, wherein said method further comprises combining an aqueous solution of an inorganic nitrite when combining said aqueous solution of nitric acid and said aqueous solution of an organic compound.

37. The mixture of claim 36, wherein said aqueous solution of nitric acid, said aqueous solution of the organic compound, and said aqueous solution of an inorganic nitrite are combined using a controlled process.

38. The mixture of claim 37, wherein said controlled process of combining the said solution of nitric acid, said aqueous solution of the organic compound, and said aqueous solution of an inorganic nitrite is an automated process.

39. The mixture of claim 38, wherein said automated process is a computer controlled process.

40. The mixture of claim 36, wherein said inorganic nitrite is selected from the group consisting of ammonium nitrite, sodium nitrite, potassium nitrite, lithium nitrite, calcium nitrite, or magnesium nitrite.

41. The mixture of claim 23, wherein said carbohydrates are selected from the group consisting of monosaccharides, disaccharides, oligosaccharides, aldonic acids, aldonic acid esters, aldonic acid lactones, aldonic acid salts, alduronic acids, alduronic acid esters, alduronic acid salts, alditols, cyclitols, corn syrups with different dextrose equivalent values, and monosaccharides, disaccharides, oligosaccharides, and polysaccharides derived from plant, microorganism, or biomass sources.

42. The mixture of claim 24, wherein said membrane filtration is nanofiltration.

43. The mixture of claim 19, wherein the monosaccharides are selected from the group consisting of D-glucose, D-mannose, D-xylose, L-arabinose, D-arabinose, D-galactose, D-ribose and D-fructose.

44. The mixture of claim 19, wherein the monosaccharides are selected from the group consisting of D-glucose, D-mannose, D-xylose and L-arabinose.

45. The mixture of claim 19, wherein the monosaccharides are D-glucose.

46. The mixture of claim 19, wherein the aldonic acid lactones are D-gluconic acid δ lactone.

47. The mixture of claim 41, wherein the monosaccharides are selected from the group consisting of D-glucose, D-mannose, D-xylose, L-arabinose, D-arabinose, D-galactose, D-ribose and D-fructose.

48. The mixture of claim 41, wherein the monosaccharides are selected from the group consisting of D-glucose, D-mannose, D-xylose and L-arabinose.

49. The mixture of claim 41, wherein the monosaccharides are D-glucose.

50. The mixture of claim 41, wherein the aldonic acid lactones are D-gluconic acid δ lactone.

* * * * *